(12) United States Patent
Sultan (10) Patent No.: US 11,532,081 B2
(45) Date of Patent: Dec. 20, 2022

(54) ENHANCED THERMAL DIGITAL SUBTRACTION ANGIOGRAPHY (ETDSA)

(71) Applicant: Hashem Sultan, Pembroke Pines, FL (US)

(72) Inventor: Hashem Sultan, Pembroke Pines, FL (US)

( * ) Notice: Subject to any disclaimer, the term of this patent is extended or adjusted under 35 U.S.C. 154(b) by 191 days.

(21) Appl. No.: 16/952,471

(22) Filed: Nov. 19, 2020

(65) Prior Publication Data

US 2022/0156920 A1     May 19, 2022

(51) Int. Cl.
*G06T 5/50*     (2006.01)
*G06T 7/00*     (2017.01)
*A61B 6/00*     (2006.01)

(52) U.S. Cl.
CPC ............ *G06T 7/0012* (2013.01); *A61B 6/504* (2013.01); *G06T 5/50* (2013.01); *G06T 2207/10048* (2013.01); *G06T 2207/20224* (2013.01); *G06T 2207/30024* (2013.01); *G06T 2207/30101* (2013.01)

(58) Field of Classification Search
CPC ............... G06T 7/0012; G06T 5/50; G06T 2207/10048; G06T 2207/20224; G06T 2207/30024; G06T 2207/30101; A61B 6/504
See application file for complete search history.

(56) References Cited

U.S. PATENT DOCUMENTS

2007/0213617 A1* 9/2007 Berman et al. .......... A61B 6/00
600/473

FOREIGN PATENT DOCUMENTS

WO    WO-2020014746 A1 * 1/2020 ......... A61B 18/1815
WO    WO-2021247460 A1 * 12/2021

OTHER PUBLICATIONS

Joseph T. Hardwicke and O. Garth Titley: "Thermographic Assessment of a Vascular Malformation of the Hand: A New Imaging Modality", Publication date: Mar. 30, 2016, Journal of Clinical Imaging Science. (Year: 2016).*

* cited by examiner

*Primary Examiner* — Siamak Harandi
(74) *Attorney, Agent, or Firm* — Christopher J Vandam, PA; Chris Van Dam (57) ABSTRACT

A method and a device for performing enhanced thermal digital subtraction angiography comprising infrared video camera, computer cable of subtracting all images produced by tissues having a temperature below a setup point, reconstructing and displaying 2D or 3D images of the received data, performing measurement of the vessels being displayed, conducting data analysis and mathematical calculation of hemodynamic parameters, storing and displaying the images produced. Said device is coupled to embodiments to warm the intravascular injectate, to warm the J-tip guide wire and to warm the intravascular catheter during angiography and during endovascular procedures.

Furthermore, the device can be used to perform non-enhanced thermal digital subtraction imaging of part of interest and enhanced thermal digital subtraction imaging for joint, epidural and intrathecal space producing thermal arthrography, epidurography and myelography.

3 Claims, 8 Drawing Sheets

ENHANCED THERMAL DIGITAL SUBTRACTION ANGIOGRAPHY (ETDSA)

BACKGROUND OF THE INVENTION

1—Field of the Invention

The present invention relates to medical imaging. Specifically, the current invention is related to image processing during angiography using enhanced warm fluids and digital subtraction of irrelevant tissues and organs.

2—Description of Prior Art

Angiography is a medical imaging technique used to visualize the inside of blood vessels with particular interest in the large and small arteries, veins and the heart chambers. This is traditionally done by injecting a radio-opaque contrast agent into the blood vessel. Different types of imaging had been in use; Fluoroscopy (Imaging can be done using X-ray based techniques), angiography, MRA (MRI angiography), radionuclide angiography (is an area of nuclear medicine which specializes in imaging to show the functionality of the heart. It involves use of radioactive agent, injected into a patient, and a gamma camera for acquisition.

The angiogram technique was first developed in 1927 by the Portuguese physician and neurologist Egas Moniz at the University of Lisbon.

In traditional angiography, images are acquired by exposing an area of interest with time-controlled x-rays while injecting contrast medium into the blood vessels. The image obtained includes the blood vessels, together with all overlying and underlying structures. The images obtained before DSA was discovered were useful for determining anatomical position and variations, but unhelpful for visualizing blood vessels accurately.

Subtraction angiography was first described in 1935 and in English sources in 1962 as a manual technique. Digital technology made DSA practical from the 1970s.

In order to remove the distracting structures to see the vessels better, first a mask image is acquired. The mask image is simply an image of the same area before the contrast is administered. The radiological equipment used to capture this is usually an X-ray image intensifier, which then keeps producing images of the same area at a set rate (1 to 7.5 frames per second). Each subsequent image gets the original "mask" image subtracted out. (Mathematically, the incoming image is divided by the mask image.) The radiologist controls how much contrast media is injected and for how long. Smaller structures require less contrast to fill the vessel than others. Images produced appear with a very pale grey background, which produces a high contrast to the blood vessels, which appear a very dark grey.

In digital subtraction angiography, DSA, the images are all produced in real time by the computer or image processor, while the contrast is injected into the blood vessels.

DSA with fluoroscopy is very rarely used today for diagnostic purpose and has been widely replaced by MRA, and CT angiography. However, the use of fluoroscopy DSA is still the main technique used for endovascular procedures such as stent placements, thrombectomy, embolectomy and with diagnostic cardiac catheterization when endovascular intervention is anticipated.

Contrast material injected intravascular may cause nephrotoxicity, allergic reactions, and many temporary side effects. Fluoroscopy and CT cannot be used in early pregnancy and can expose all patients to high radiation dose.

Thermal imaging's use in medicine had been very limited due to the fact that its images are hard to read due to the fact that IR images are inherently vague and unclear in nature. Very little progress had been made in this field despite the fact that IR camera was first invented in 1929 by Hungarian physicist Kalman Tihany as (night vision) electronic television camera for anti-aircraft defense in Britain.

Originally developed for military use during the Korean war, thermographic cameras have slowly migrated into other fields. More recently, the lowering of prices has helped fuel the adoption of infrared viewing technology. Advanced optics and sophisticated software interfaces continue to enhance the versatility of IR cameras. Its used has been widely implemented in law enforcement and anti-terrorism field, data center monitoring, astronomy, chemical imaging and in almost every filed of technology. However, its use in medical field did not match its use in other fields.

Turnidge, in his U.S. Pat. No. 4,995,398, dated Feb. 26, 1991, describes thermal coronary angiography during surgery, to determine the patency of the blood vessel graft following the completion of the distal anastomosis of the graft.

Japanese patent No. JP3565851B2, published on Sep. 15, 2004 describes infrared angiography system used in cardiovascular surgery taking advantage of routine use cooling the blood during the bypass surgery to obtain better infrared image of the blood vessels. However, the image was limited in its clarity due to lack of subtraction of the images of the surrounding tissue. Furthermore, this technique is limited to gastric bypass surgery when the blood is cooled to a very low degree to stop the heart from pumping during surgery. The patent incorporates a CCD (charged-coupled device) video camera. The images of both IR camera and CCD camera are both displayed in a split screen.

Prokoski, in his U.S. Pat. No. 8,811,692 B2 dated Aug. 19, 2014 and in his U.S. Pat. No. 8,463,006 B2 dated Jun. 11, 2013 describes a system using calibrated infrared and range imaging sensors to produce a true 3D surface model of any body region within the fields of view of both sensors. The invention system provides an enabling technology for searchable image libraries. His invention describes the use of the IR images of the superficial vascular anatomy of a person as biometric identification. Furthermore, he describes the advantage of using his system in evaluating pressure ulcer and wound care management.

Cai et al, in his US publication No. US2020/0120291 A1, dated Apr. 16, 2020, describes a system for a Near-infrared Fluorescein for fluorescein angiography include a near-infrared continuous laser emitting source, near infrared camera and color camera connected to a terminal display Chinese patent application No. CN104434033A dated Mar. 25, 2015 describes a near-infrared angiography to superficial blood vessels and to treat spider veins of skin.

Japanese patent No. JP2019213873A published on Dec. 19, 2019 describes a method using ICG-NIR-FAI, Indocyanine green (ICG) near-infrared (NIR) fluorescence angiography, for displaying, analyzing, and quantifying angiography, and the change in angiography and perfusion during surgical procedures before and after revascularization.

Moreno, in his U.S. Pat. No. 6,816,743 B2, dated Nov. 9, 2004, describes an apparatus for analyzing the chemical composition of vulnerable plaques with an intravascular catheter having a near-infrared light source.

Rahimian, in his U.S. Pat. No. 10,391,277 B2 dated Aug. 27, 2019, describes a device for catheterization through Angio-navigation to treat disease areas through direct imaging using tracking such as RF, IR, or US, of the catheter through the patient's vascular anatomy. The direct image is to be assisted with at least one of MRI, CT, or 3DRA imaging to generate a stereotactic coordinate system and in room global positioning system (GPS).

Mohamed, in his U.S. Pat. No. 8,060,186 B2 dated Nov. 15, 2011 a method for guiding stent deployment during an endovascular procedure using C-arm mounted X-ray apparatus.

Chinese Patent No. CN109381205, dated Feb. 26, 2019 describe a method for executing the digital subtraction angiography by subtracting mask images data set and using X-ray imaging.

Steinberg, in his U.S. Pat. No. 9,014,453 B2, and Cohen in his patent No. 10,226,178 B2 dated Mar. 12, 2019, describe an automatic angiogram detection by determining an extent to which pixels within the image frame are likely to correspond to the blood vessel using fluoroscopy.

Shreibe, in his U.S. Pat. No. 9,275,437, dated Mar. 1, 2016 describes a system and a method for performing DSA which does not require a non-enhanced or mask image to be obtained.

European patent No. EP 3 223 704 B1, dated May 22, 2019, and patent EP 3 242 597 B1 dated Jul. 11, 2018, provide a method for cardiac digital subtraction angiography by obtaining cardiac and breathing phase image and by subtracting mask images using fluoroscopy.

Wang, in his US patent application No. U.S. Pat. No. 5,827,187 dated Oct. 27, 1998, describes a MRI digital subtraction angiography similar to X-ray-DSA using a mask selected image without contrast.

Till today, there have been very slow progress in implementing and using thermal images in medical practice and very little progress had been made in this field despite the fact that IR camera was first invented in 1929. This is due to the fact that its images are hard to read because IR images are inherently vague and unclear in nature. The citations mentioned in this application are inadequate attempts to make a good use of this amazing technology.

There is still more need for a device that can help physicians perform diagnostic angiography and endovascular procedures with clarity, portability option so that angiography can be performed at bedside, or in in a medical office setting, ease of use, with no harm to the patients from radiation or injection of potentially harmful contrast.

The current invention overcome most of disadvantages and the drawbacks of the currently used angiography techniques.

SUMMARY OF THE INVENTION

The current invention, ETDSA, advances into the medical field a technology that have been in a market for a century, a technology which is safe to the patient, cheaper to use, and can be used for both diagnosis and for endovascular treatment.

The present invention discloses a method and a system to perform digital subtraction angiography, DSA, of a thermal video imaging without taking a mask image or injecting a potential harmful contrast medication.

The current invention incorporates a computer (microprocessor, software, memory, and other components well known to ordinary person in the computer art), cable of subtracting all colors and images produced by tissues having a temperature below a temperature setup point, capable of performing data analysis, reconstructing and displaying 2D or 3D images of the data, capable of measuring the length and the internal diameter of the lumen of the vessels being displayed, conducting data analysis and mathematical calculation of hemodynamic parameters, storing and displaying the images produced.

The device is coupled to heating components for warming the intravascular fluid injectate, and for warming the J-tip guide wire and the intravascular catheter during angiography and endovascular procedure. The fluid injectate is usually Lactated Ringer or Normal Saline.

In the preferred embodiment, the computer is coupled to a temperature sensor incorporated in a control unit which controls the flow and delivery of the warm fluid to the patient. It monitor the fluid temperature and alarm the operator if the fluid temperature dropped below a set-up point.

In the preferred embodiment, the intravascular catheter is preferably incorporating a heat-conducting wire embedded in its wall and in its tip. Warming this wire will allow ideal visualization of the catheter.

Furthermore, in the preferred embodiment, a battery-operated heater is disclosed to allow constant warming of the intravascular catheter and the guide wire to a level above the maximum body temperature.

The general object of this invention is to improve the quality of thermal images acquired during angiography. This improvement will allow thermal image technology to be an additional option to X-ray angiography and CT-angiography. An alternative option to these two methods is essential in patients with chronic renal disease, in patients allergic to a contrast agent, and in pregnant women.

The current invention, ETDSA, enable physicians to obtain images of the interested area from different angles simultaneously; anteroposterior, right and left lateral and right and left oblique views by having multiple thermal cameras mounted on semicircular arc attached to the ceiling of the operating room, or mounted to a mobile holder.

The current invention, ETDSA has an additional useful advantage over CT or X-ray when emergency angiogram is needed for pulmonary circulation. Pulmonary angiogram does not need arterial catheterization. Central venous catheter or even Peripheral I-V line is sufficient. This advantage is of utmost important in cases of acute chest pain secondary to pulmonary embolism. Pulmonary angiogram can be done at the bed side by simply mounting the whole system over a movable trolley or simply carrying the device in a case. The patient's peripheral IV or central line can be used to deliver warm fluid through the right ventricle to the pulmonary artery and the pulmonary circulation. ETDSA allow every physician, in ER, ICU, hospital floor, or even in a medical office to perform emergency pulmonary angiogram without wasting any critical time waiting for the radiologist on call and his staff to arrive to the hospital.

Another objection of the current invention is its capability to perform arthrogram in an office setting. Injecting warm sterile fluid above the body temperature in a joint such as the knee will enable the examining physician to obtain a detailed demonstration of the joint cavity and any anatomical pathology. Another application of this invention is the use of thermal digital subtraction technique described in this application without thermal enhancement for bone imaging.

Another object of the current invention is to provide safe, reliable, easy to use, low cost, portability option, displaying vascular images in colors or in W/B, images in 2d or 3D options, ability to measure the diameter and the volume of a specific vessel, and the ability to measure the flow rate and the resistance and the pressure differences by calculating the temperature difference over time, dT/time and by using other hemodynamic parameter entered into the device by the physician.

The foregoing and other objects and advantages of the invention will appear from the following description. In the description, reference is made to the accompanying drawing which from a part hereof, and in which there is shown by way of illustration a preferred embodiment of the invention. Such embodiment does not necessarily represent the full scope of the invention, however, and reference is made therefore to the claims herein for interpreting the scope of the invention.

DETAILED DESCRIPTION OF THE PREFERRED EMBODIMENTS OF THE INVENTION

The current availability of the digital technology and science made it possible today to make further advance in the use of thermal images. As mentioned earlier, the application of thermal imaging in the field of medicine had been very limited mainly by its inherent nature of poor quality of images it produce, by the overlapping of images produced by the tissues surrounding the area of interest and by the difficulty in interpreting the images due to its complexity. Furthermore, the availability of high-quality imaging techniques such as MRI, CT, fluoroscopy, PET scan, ultrasound, made the interest in thermal imaging in medicine almost zero.

The current invention will put thermal imaging technology in its proper place in the medical field. This will give physicians more imaging options and provide additional advantages that other technology cannot offer. Example of such an additional advantage is that no other current technology can offer is arthrography and pulmonary angiography in an office setting on in hospital floor without bulky X-ray machine.

Figure 1:
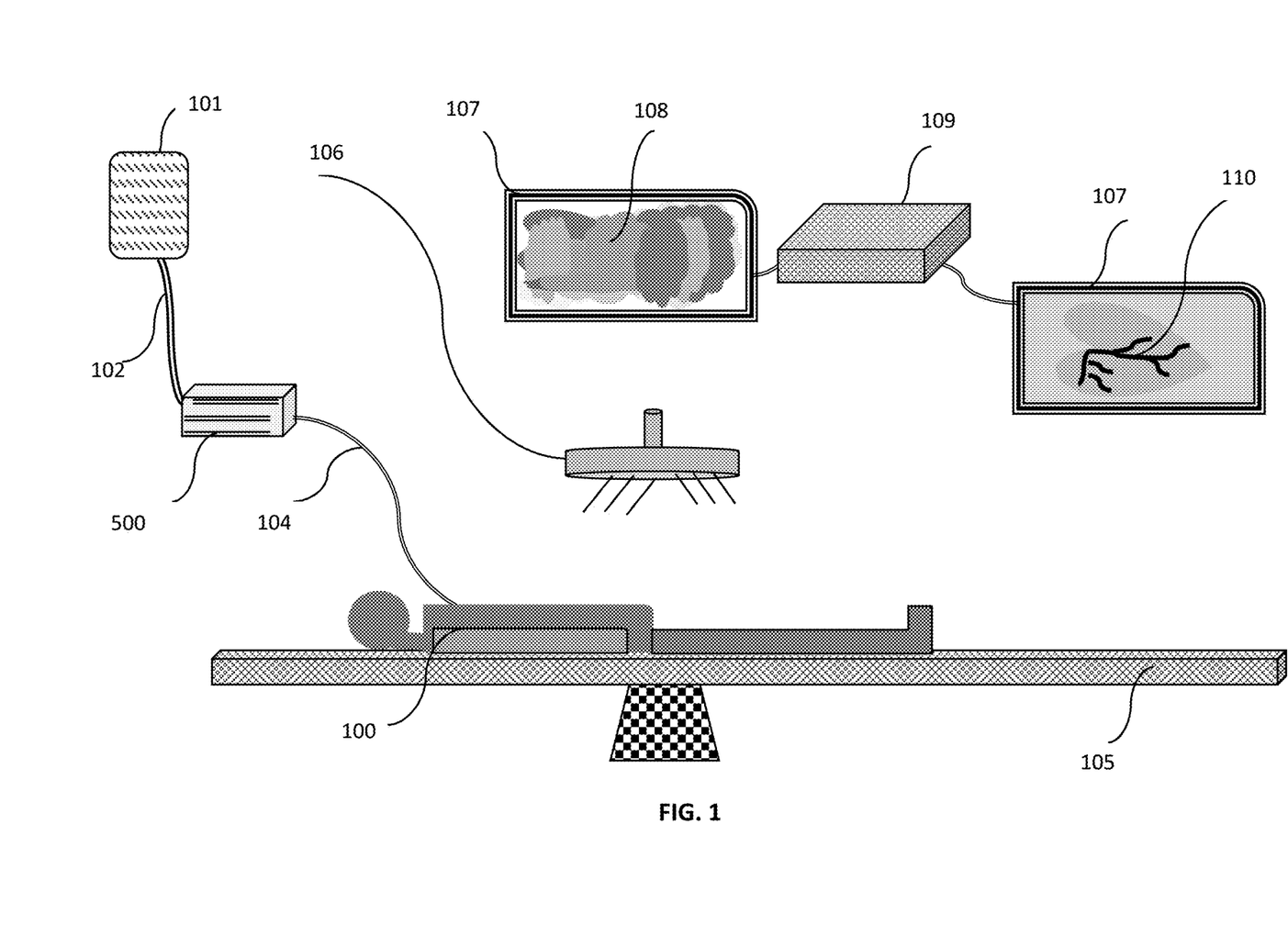
FIG. 1 is a schematic view of the main components of the invention in procedure room setting.

FIG. 1 describes the main embodiments of the device. For illustration, a patient 100 is shown lying on an operating table 105. I.V fluid bag 101 such as normal saline or lactate Ringer is attached to the patient via IV tubing 102 normally used in hospital and in any medical facility. The tubing 102 is connected to a fluid warmer 500. Which will be described in further details below. After being warmed the IV fluid will pass through conducting IV tubing 104 to the intravascular catheter which is inside the patient's arterial or venous vessel depending on the procedure. Intravascular catheter is usually placed intraarterial if the is the area of interest is in the systemic circulation, and the catheter is placed intravenous if the area of interest is in the pulmonary circulation.

At least one TIC 106 (thermal imaging camera) is used to capture the images of the targeted area during the injection of the warm fluid. Selecting proper TIC for angiogram is very critical. The greater the thermal sensitivity of the camera the better its resolution. Other factors need to be considered in choosing the correct TIC for the purpose of this invention.

Human eyes are only sensitive to the range that is between wavelength 380-780 nanometers in length. Infrared radiation (IR), on the other hand, has wavelengths above red visible light between 780 nm and 1 mm. IR is categorized as IR-A (780 nm-1.4 µm), IR-B (1.4-3 µm) and IR-C, also known as far-IR (3 µm-1 mm).

TIC detect infrared radiation given off by an object. Infrared radiation is emitted by all objects based on their temperature, so the resulting image (called a thermogram) allows one to see variations in temperature. Also known as thermal imaging, the technology has been used in a variety of ways: at airports to detect swine flu cases during the 2009 pandemic, by firefighters to see through smoke and locate persons, by maintenance workers to identify overheating parts and heat leaks, and in studies of physiological processes in humans and animals. In fact, all objects that have a temperature above absolute zero emit heat and this heat can be detected by thermal imaging.

Thermal Imaging, or Infrared Thermography, is a non-contact technology that measures or "sees" infrared wavelengths emitted from objects, and then converts the temperature information into an image. The image features a color palette that represents a temperature range of the image displayed.

In any thermogram, the brighter colors (red, orange, and yellow) indicate warmer temperatures (more heat and infrared radiation emitted) while the purples and dark blue/black indicate cooler temperatures (less heat and infrared radiation emitted).

Thermal sensitivity, or Noise-Equivalent Temperature Difference (NETD), measures the smallest temperature difference that a TIC can detect in the presence of electronic circuit noise. Cameras with a low NETD will detect smaller temperature differences and provide higher resolution images with increased accuracy. Thermal sensitivity is measured in milli Kelvins (mK). Cameras are more sensitive with values at the low end of the scale. For example, cameras with 50 mK are about 4 times as sensitive as a camera with 200 mK. The more sensitive (50 mK) cameras provide a wider temperature difference, resulting in more colors on the thermal display.

Most of the cameras can detect temperature differences of 1° C. or better. FLIR (Forward-Looking Infrared) company offers a wide range of R&D cameras that can distinguish temperature changes as subtle as 0.02° C. in a temperature range from −80° C. to +3,000° C. (−112° F. to +5,432° F.).

The temperature range indicates the minimum and maximum temperatures that a camera can measure. As an example, FLIR K-Series cameras accurately measure temperatures between −20° C. and +650° C. (−4° F. to +1,202° F.). Maximum high temperatures come at the expense of image quality.

The TIC camera 106 in the preferred embodiment must have a small temperature range preferably between 30-70 degree centigrade and very low sensitivity to detect a subtle difference of temperature lower or equal to 0.02-degree Centigrade. Although, theoretically 3D images are more informative than 2D images, physicians, in general, are much more familiar with 2D images and are expert in mentally constructing the 3D image of the blood vessels by studying AP and lateral views only. Adding oblique view in 2D image will eliminate the need for 3D imaging. The preferred embodiment in this invention is a 2D camera, however, 3D camera can be used, and their use is included in this description.

At least one TIC 106 (thermal imaging camera) is used to capture the images of the targeted area during the injection of the warm fluid. As will be described below, the preferred embodiment comprises more than one TIC. The images of the multiple TICs are taking simultaneously during the injection.

A computer 109 is incorporated in the system. It is an essential component of the system. No detailed descriptions of the embodiment of the computer 109 will be described here, since descriptions and specifications are well known to the ordinary person in the computer field. In short, the computer 109 receives and processes the images taking by the TICs and subtract all the data related to the colors produced by the surrounding and overlapping tissues. The resulted DSA images are displayed on a screen 107. Multiple images that were taken simultaneously by all the TICs are displayed on split screen solitary screen 110 or different projections are displayed on multiple adjacent screens. Screen does not display the original image before subtraction. However, the computer may display the original image 108 if there was a need to review it for whatever reason. Pre-subtraction images are useless, misleading and cannot be properly interpreted.

Although the screen resolution of the display screen 107 plays some part in the image quality, the detector resolution, TIC resolution, plays a pivotal role in image quality of thermal imaging cameras. Higher resolutions provide precise and reliable measurements of smaller target, creating sharper thermal images. The higher the detector resolution, the more accurate the camera.

When evaluating between detector resolution and display resolution, we need to know that the quality of the thermal image and its data is always determined by the detector resolution. For example, if the built-in screen has a resolution of 307,200 pixels (640×480) but the thermal detector resolution is only 19,200 pixels (160×120), the thermal image can only be measured by the resolution of the thermal detector.

Figure 2:
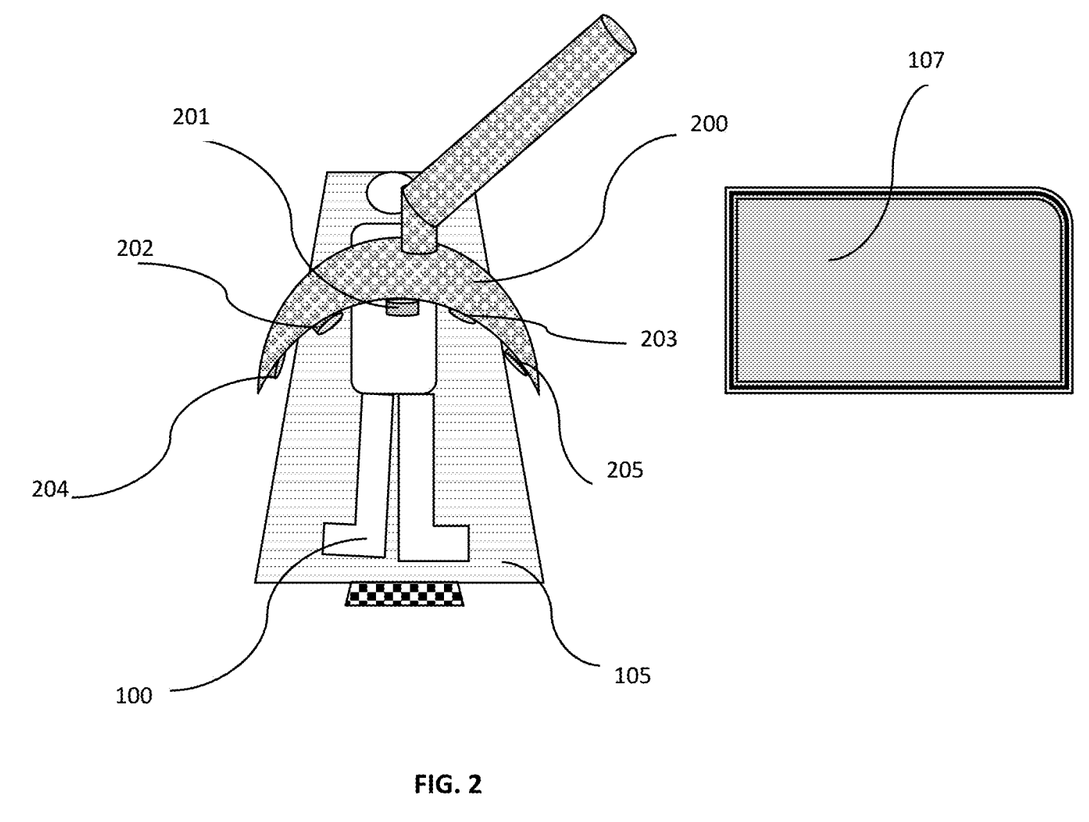
FIG. 2 is a schematic view of multiple thermal cameras mounted on semicircular arc.

FIG. 2 illustrates the preferred embodiment of mounting the TICs on the projector 200. Depends on the operating room setting, the projector 200 can be mounted to the ceiling or can be mounted on a mobile carrier similar to the C-arm in fluoroscopy. The projector 200 is preferably semicircular in shape, its diameter can be increased or decreased in a telescopic method to accommodate the size of different patients in order to keep TICs in optimal distance from the patient.

Camera 201 for A-P imaging, camera 202 and camera 203 for right and left oblique view, and cameras 204 and 205 for right and left lateral view respectively. All cameras are turned on and off by one control switch. More studies are needed to determine the optimal number of TICs that gives best imaging results and least cost. For example, only AP camera and one lateral camera may be adequate.

Figures 3A, 3B:
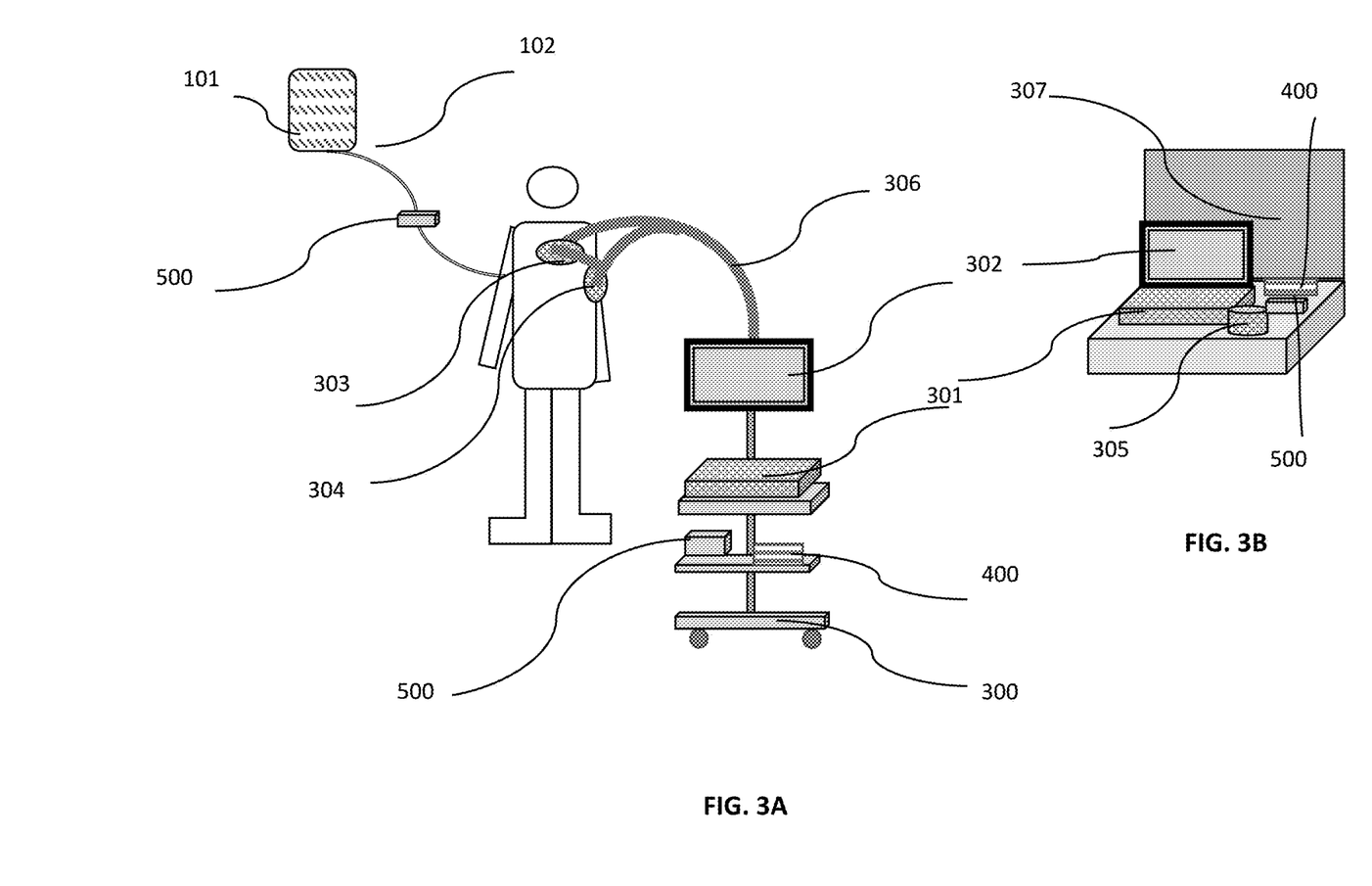
FIG. 3A is a schematic view of the mobile version of the invention.
FIG. 3B is a schematic view of the portable version f the invention.

FIG. 3A Illustrates the mobile version of the invention. In this version, all embodiments of the invention are place on a mobile cart 300. The cart will have on its shelf the computer 301, which is identical in description to the computer 109 in FIG. 1. However, the only optional difference is that the display 302 can be either mounted on the cart separately as separated monitor or the display 302 can be incorporated within the computer 301 in a very similar way to laptop versus desktop is configured.

TIC 303 and 304 represent A-P and lateral cameras that are mounted on semicircular arm 306. Depends on the medical facility and its needs, the semicircular arm 306 may have any number of TICs.

FIG. 3B illustrates the portable version of the invention. In this version, all embodiments of the invention are place in a carry-on case 307. One or two TICs camera 305, the computer 301 (a laptop version), the fluid warmer 500 and the coiled IV tubing 400 are kept in the carry-on case 307. When in use, the cameras will be held manually. Two cameras are preferable. Two cameras will enable user to take simultaneously A-P and latera view.

This portable version is suitable for medical offices where bulky machine with semicircular arm is not convenient. Simultaneous A-P and lateral views, in this portable version, requires a second hand. Two assistants are needed to hold the TICs in proper location. Both cameras are controlled by the same switch. In the preferred embodiment, the on/off activation is from the computer's keyboard. Warm fluid to a temperature has to be injected while taking the images. Fluid warmer 500 should be attached to the IV tubing as described below.

Figures 4, 5:
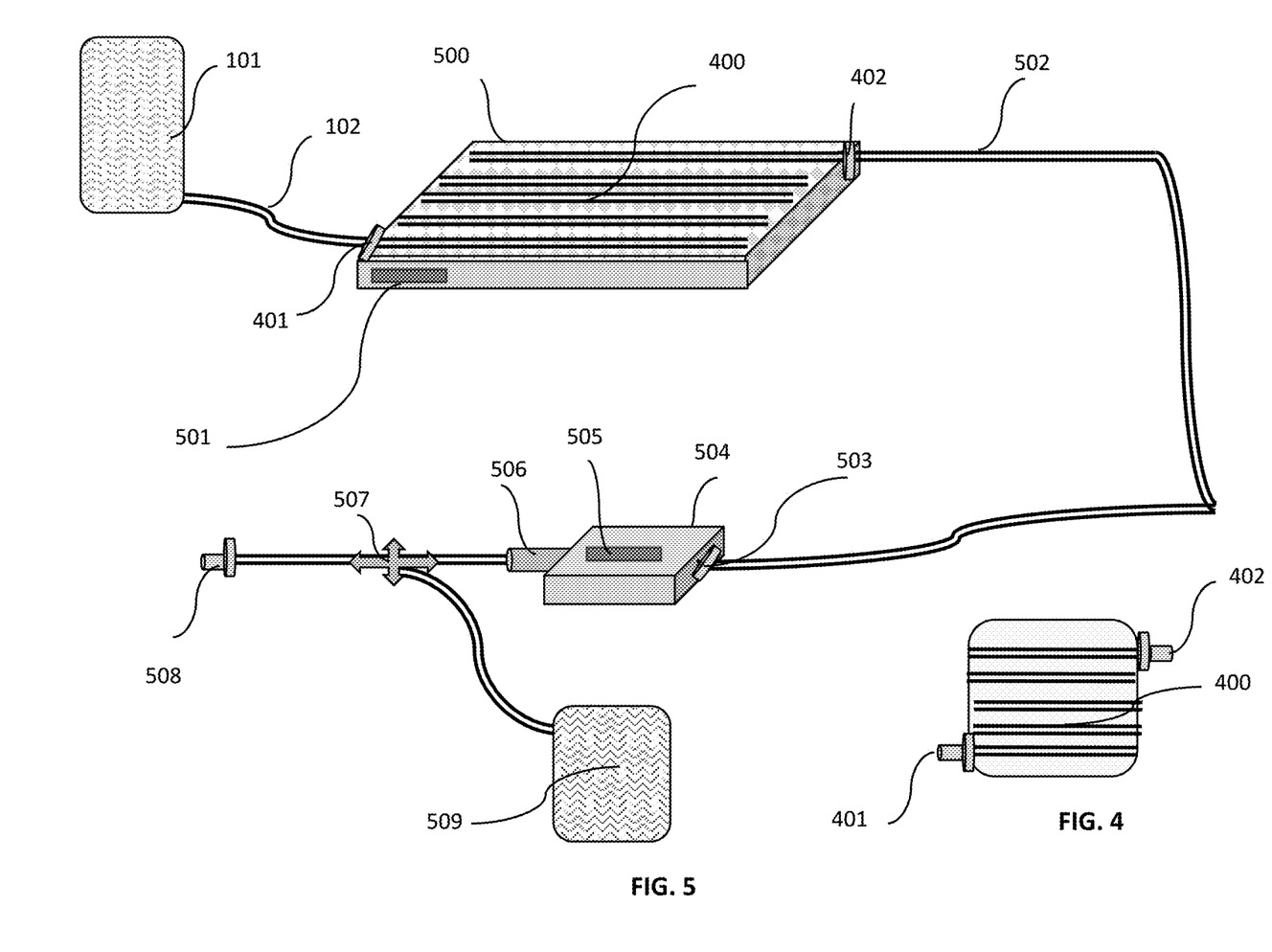
FIG. 4 is a schematic view of coil tubing with proximal and distal connectors.
FIG. 5 is a schematic view of the fluid warming system.

FIG. 4 and FIG. 5 describes the preferred fluid warming embodiment of the device. A fluid bag 101 contains sterile IV fluid such as normal saline or Lactate Ringer attached to a regular IV tubing 102. Tube 102 is connected to a coiled regular size IV tubing 400 by a connector 401. The coiled tubing 400 is placed in a warming box 500. The warming box 500 can be powered by incorporated batteries or by being plugged to electricity outlet. A temperature control panel 501 to adjust the level of the heating process. The warming box 500 operates in a very similar wat to a known toaster (embedding resistant coils).

The distal end 402 of the coiled tube 400 is attached to a conducting tube 502 of the warm fluid which has at its end a connector 503 connecting 502 to a flow controller 504. The flow controller has a control panel 505 operated by the physician or his assistant to turn on or off the flow of the warm fluid and to control the volume of the warm fluid that can be delivered. The flow controller incorporates a temperature sensor 506. If the fluid temperature is below the set-up value, the sensor 506 will send a warning signal to the computer 109. The set-up temperature minimum and maximum is entered into the computer 109/301 before the start of the procedure. Any signal from the temperature sensor 506 indicating that the fluid temperature is below the set-up points, an alarm will set off. This will usually happen when the fluid in the conducting tube 502 gets cold because of the delay in the preparation to start or continue the procedure for any reason.

When the fluid gets cold and the alarm sets off, cold fluids in tube 502 needs to be discarded. A switch 507 can be turned so that the cold fluid is directed towards a collecting bag 509. The switch 507 needs to be very close to the distal connector 508. The distal connector 508 is for connecting to the intravascular catheter, arterial or venous depending on the procedure.

Systemic arterial angiography is used for cardiac catheterization, renal angiography, mesenteric angiography cerebral angiography and endovascular procedures such as stent placements and embolectomy or thrombectomy. The first step in the procedure after patient preparation is the insertion of the intravascular introducer. The introducer is usually place in the Femoral artery or the Radial artery. Through this introducer a 150-cm length of a 0.035-in. J-tip guide wire is commonly used.

Figure 6:
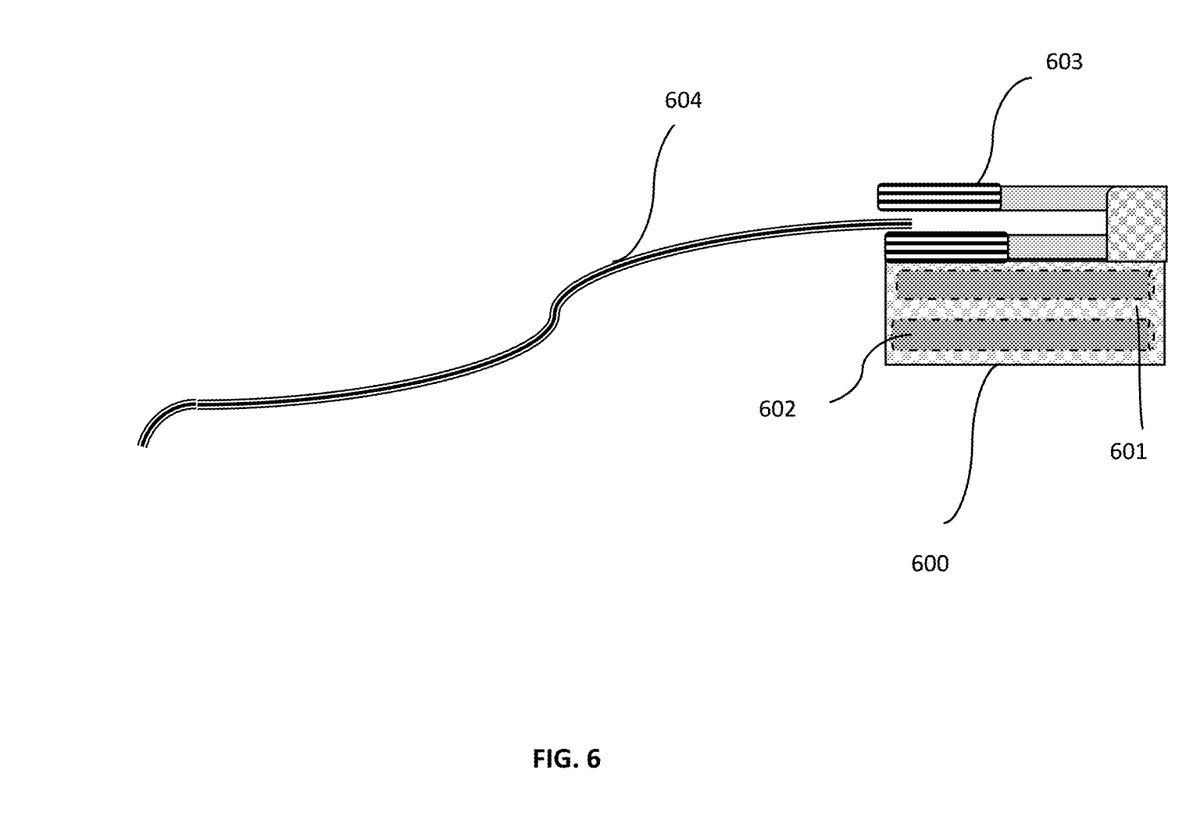
FIG. 6 is a schematic view of the guide wire warming component.

FIG. 6 describes a small portable warmer 600 to the J-tip guide wire 604. The heater comprises battery compartment 601 for batteries 602 and heating elements 603. The size and shape of the device is similar to the finger pulse oximeter. The straight end of the guide wire is warmed to better visualize the wire. All catheters and sheaths are advanced over a guide wire. All the currently available catheters can be used with this invention, however the catheter described below is preferred for use with this invention.

Figure 7:
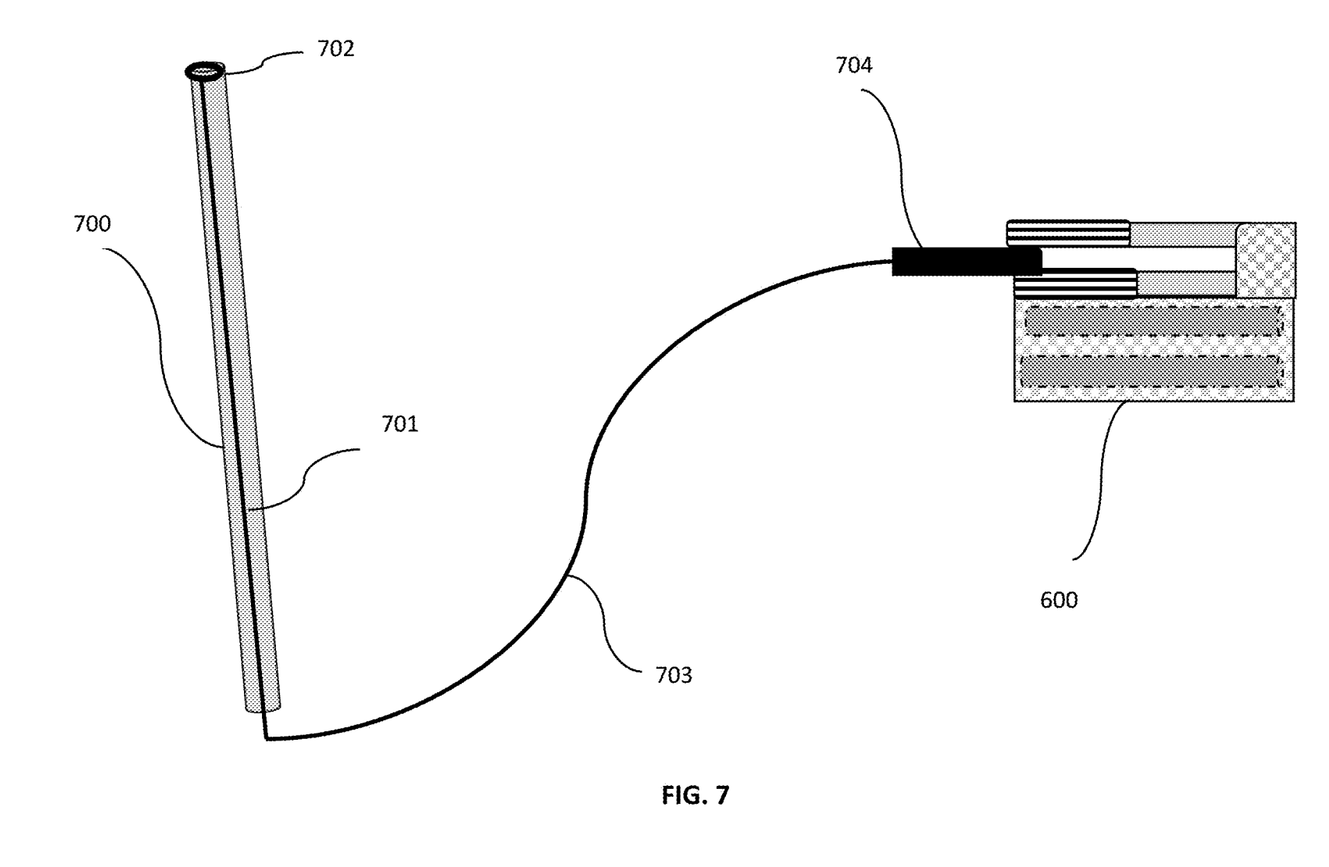
FIG. 7 is a schematic view of the preferred catheter and the warming component.

FIG. 7 disclose a preferred catheter 700. This catheter 700 has thin heat-conducting wire embedded in the wall of the catheter 701 and embedded in its distal orifice 702. The heat conducting wire has two proximal portions 703 and 704. Portion 703 is simply an extra length of the heat conducting wire outside the body of the catheter 700. Portion 704 is s small plate made of the same conducting material as the wire 701. The Plate 704 can be heated using the same heater 600.

Pulmonary arterial angiography is done by placing a catheter inside the vein, preferably a central line with its tip inside the right ventricle such as a central IV catheter or Swan-Ganz catheter, in order to get ideal imaging. Since no harmful contrast material will be injected with this invention, pulmonary angiography can be done by using a standard large bore peripheral IV catheter.

Figure 8:
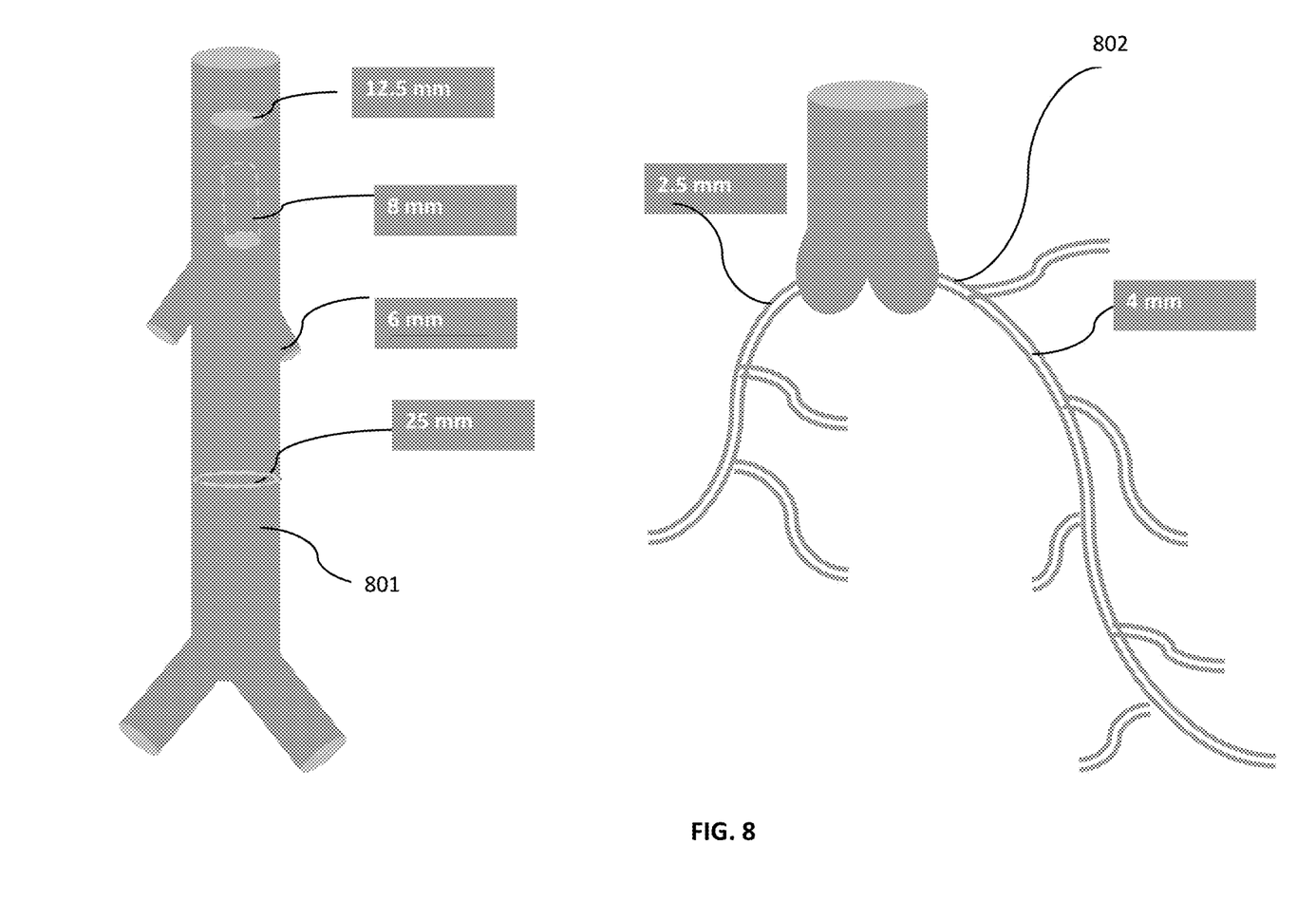
FIG. 8 is a schematic illustration of an example of displayed images of normal coronary arteries and abdominal Aorta.

FIG. 8 is a schematic illustration of an example of displayed images of normal coronary arteries 801 and normal abdominal Aorta 802.

Figure 9:
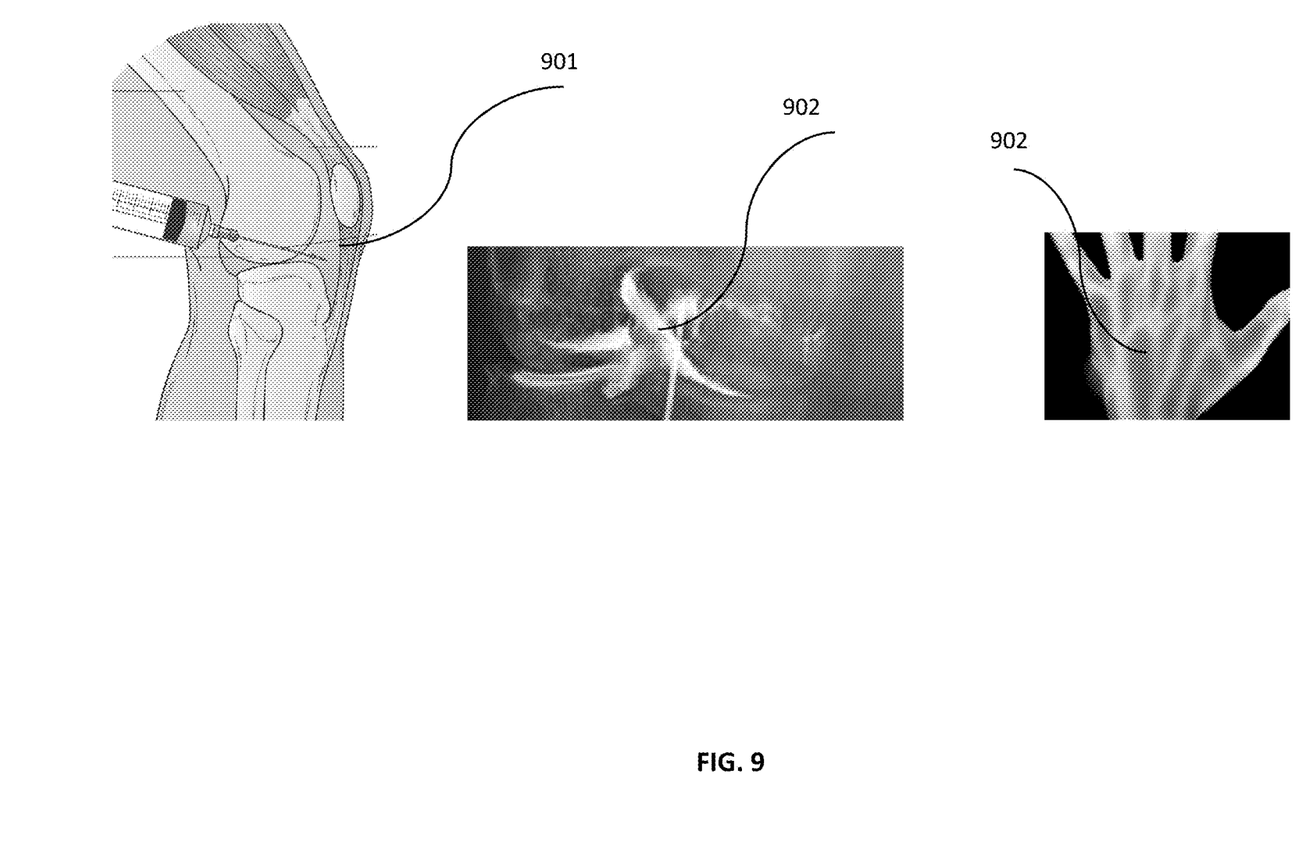
FIG. 9 is a schematic illustration of an example of displayed images of enhanced thermal digital subtraction knee arthrography, and non-enhanced thermal digital subtraction of a hand showing cold structures such as bones.

FIG. 9 illustrates another application of enhanced thermal digital subtraction angiography in performing arthrography. The application can be used to scan any part of human body's cavity such as epidural space to perform enhance digital subtraction epidurography, or intrathecal to perform enhanced thermal digital subtraction myelography.

The biggest advantage of the portable version of this invention is the ability to use it in any medical office setting. FIG. 9 illustrates some of the multiple use of the invention. In the illustration, a knee joint 901 with a needle to enter the joint. After entering the joint small amount of warm fluid above the body temperature is injected into the joint. The thermal camera sans the knee and the device digitally subtract the image of the surrounding tissue creating a perfect image of the joint space, arthrogram. image 902 is shown as an illustration of what the image will typically shows by using the current invention.

Another application of this invention is the use of the digital subtraction technique described in this application without injecting warmer fluids, without thermal enhancement. Human bones have relatively much cooler temperature relative to surrounding tissues and to its bone marrow. Bones have much less vascularity than the surrounding tissues and the bone marrow. Since the market had already developed IR cameras that can distinguish temperature changes as subtle as 0.02° C., and since bones have relatively much cooler temperature relative to surrounding tissues said digital subtraction method described in this invention can be applied to scan bone for fracture, deformity or any other pathology. FIG. 9 shows a non-enhance thermal image of a hand 903. Using very sensitive thermal camera and apply digital subtraction described above can produce images of almost same quality as X-ray. The advantage of portability, low cost, ease of use, and no radiation provide several advantages.

Although the description of this invention describes its use in humans, its use and intention of use is not limited to human being. It can be used by veterinarian on different animals.

Although the description above contains many specifies, these should not be constructed as limiting the scope of the invention but as merely providing illustration of some of the presently preferred embodiments of this invention.

I claim:

1. A device for thermal angiography and endovascular procedure comprising; at least one Thermal Imaging Camera (TIC); a computer configured for receiving and processing all the images received from said TIC(s); said computer is configured for performing digital subtraction by subtracting all images received from structures having a temperature below a set-up point and displaying all other images received from structure having a temperature above said set-up point, configured for analyzing and displaying hemodynamic parameters and blood vessel dimensions and configured for receiving temperature information from a thermal sensor; a fluid warming embodiment comprising a heater, coiled IV fluid tube, thermal sensor, a fluid flow controller.

2. A method for thermal angiography and endovascular procedure comprising; a fluid warmer configured for delivering warm fluid, above the patient's maximum normal body temperature, to an endovascular catheter; at least one camera, TIC, capturing the image of the intravascular flow of said warm fluid; a computer receiving images from said TIC(s), processing and subtracting all said images below the maximum normal body temperature of the patient; processing and displaying said images above the maximum normal body temperature, analyzing and conducting hemodynamic calculation including anatomical measurements of the blood vessels.

3. A device for thermal digital subtraction imaging of living object comprising: at least one highly sensitive Thermal Imaging Camera (TIC); a computer configured for receiving and processing all images received from said TIC(s); said computer is capable of performing digital subtraction by subtracting all images received from structures having a temperature beyond a set-up temperature range and displaying all other images received from structure having a temperature in the set-up range.

* * * * *